United States Patent [19]
Schnell et al.

[11] Patent Number: 6,113,062
[45] Date of Patent: Sep. 5, 2000

[54] SQUEEZE CLAMP

[75] Inventors: William J. Schnell, Libertyville, Ill.; David S. Utterberg, Seattle, Wash.

[73] Assignee: DSU Medical Corporation, Las Vegas, Nev.

[21] Appl. No.: 09/238,767

[22] Filed: Jan. 28, 1999

[51] Int. Cl.[7] .............................. A61M 39/28; F16K 7/04
[52] U.S. Cl. .................................................................. 251/10
[58] Field of Search ........................................ 251/4, 9, 10

[56] References Cited

U.S. PATENT DOCUMENTS

| | | |
|---|---|---|
| 3,204,636 | 9/1965 | Kariher et al. . |
| 3,698,681 | 10/1972 | Lacey ........................................... 251/10 |
| 3,713,622 | 1/1973 | Dinger . |
| 3,942,228 | 3/1976 | Buckman et al. . |
| 4,235,412 | 11/1980 | Rath et al. ................................... 251/10 |
| 4,266,751 | 5/1981 | Akhavi . |
| 4,588,160 | 5/1986 | Flynn et al. .................................. 251/10 |
| 4,643,389 | 2/1987 | Elson et al. . |
| 4,673,161 | 6/1987 | Flynn et al. .................................. 251/10 |
| 5,035,399 | 7/1991 | Rantanen-Lee ............................. 251/10 |
| 5,083,741 | 1/1992 | Sancoff ........................................... 251/9 |
| 5,174,477 | 12/1992 | Schafer ....................................... 251/10 |
| 5,203,056 | 4/1993 | Funk et al. .................................. 251/10 |

*Primary Examiner*—Kevin Shaver
*Assistant Examiner*—Eric Keasel
*Attorney, Agent, or Firm*—Garrettson Ellis Seyfarth Shaw

[57] ABSTRACT

A squeeze clamp for flexible tubing comprises a strip of plastic which is bent back on itself so that the ends are adjacent to each other. The strip defines a pair of spaced apertures to permit a flexible tube to extend through and be carried by the clamp. First and second latches at the respective ends can hold the clamp in a closed position, or it can spring outwardly into an open position. The apertures extend laterally through a first side edge of the strip, with the apertures thus being each located next to a narrow strip portion connected to wider strip portions on either side of the narrow strip portion. At least one of the narrow strip portions extends laterally outwardly beyond the side edge of the rest of the plastic strip for strengthening of the narrow strip portion, to reduce problems of involuntary twisting or torsion as the clamp is closed.

11 Claims, 3 Drawing Sheets

SQUEEZE CLAMP

BACKGROUND OF THE INVENTION

Squeeze clamps for flexible tubing, such as the well known Halkey-Roberts clamp, are commonly used in the medical field in sets for conveying medical fluid and blood to and from a patient. For example, Buckman et al. U.S. Pat. No. 3,942,228 shows a squeeze clamp similar to the known Halkey-Roberts clamp in which the clamp comprises a strip of plastic which is bent back on itself, so that the ends of the clamp are adjacent to each other. The clamp has open tube apertures, to permit it to be laterally placed onto flexible tubing and used to permit the opening of flow, or the blocking of flow, through the tubing as may be desired.

Other clamps of similar design are known, but in which the flexible fluid flow tube passes through closed apertures, such as the design specifically shown in Utterberg U.S. Pat. No. 08/943,672, filed Oct. 3, 1997, and many other similar clamp designs.

It is often desirable to have a clamp with the open tube apertures connected laterally to the exterior by slots as in the Buckman et al. U.S. Pat. No. 3,942,228, so that the clamp can be subsequently added to a manufactured tubing set when that is desired. Clamps which have laterally closed tubing apertures without side slots must of course be threaded or strung onto the particular tubing which carries them in the manufacturing process, usually before the ends of the tubing are attached to a component, preventing addition of the clamp.

However, as a disadvantage, clamps in which the tubing apertures have side slots for lateral connection are thus weakened thereby, since the remaining portion of the strip that is laterally adjacent to the side slot is substantially narrowed and thus weakened by the presence of the side slot and aperture. This can interfere with the function of the squeeze clamp.

While one could simply widen the entire strip that forms the clamp to accommodate this, that provides an overall enlargement to the squeeze clamp which can result in the need for larger packaging when the clamps are packed with a tubular set. This is of course undesirable.

In accordance with the invention, squeeze clamps are provided which utilize side slots connecting to their tubing apertures so that the clamps may be laterally placed onto flexible tubing, and do not need to be threaded onto the tubing from the ends thereof. Nevertheless, these clamps, although overall no wider than corresponding clamps having closed tube apertures without side slots, can still exhibit good quality dynamic action largely free of involuntary torsion or lateral twisting of the clamp, as one attempts to close it, because of weakness of the clamp adjacent the tube apertures with their side slots. According, the clamps may be packaged with sets in a typical coiled form without a need to significantly enlarge the packaging, since the clamps remain overall of the same size as present conventional Halkey-Roberts clamps. However, they have the added advantage of being laterally applicable to flexible tubing of manufactured sets when and as desired.

DESCRIPTION OF THE INVENTION

By this invention, a squeeze clamp for flexible tubing is provided having open and closed positions for allowing flow through the tubing or preventing such flow. The squeeze clamp comprises a strip of plastic having first and second opposed side edges and first and second ends. The strip is bent back on itself, in its natural, unstressed position, so that the ends of the strip are adjacent to each other, in the typical manner of clamps that resemble Halkey-Roberts clamps. The strip defines a pair of spaced apertures to permit a flexible tube to extend through and be carried by the clamp.

The apertures extend laterally through the first side edge of the strip. Thus, the apertures are each located next to a narrow strip portion which is connected to wider strip portions on either side of the narrow strip portion. This of course is a consequence of the existence of the spaced apertures and their lateral slots through the first side edge of the strip, leaving only a portion of the width of the strip intact.

In accordance with this invention, the narrow strip portion adjacent to at least one of said apertures extends laterally outwardly beyond the second side edge of the rest of the plastic strip, to strengthen the narrow strip portion without significantly adding to the overall width of the entire squeeze clamp. Thus, involuntary torsion or lateral twisting can be reduced or avoided as the clamp is opened and particularly closed, while at the same time the clamp can be laterally applied to intact tube sets without being threaded over an end thereof.

Preferably, the one narrow strip portion described above is located adjacent to an area where the strip bends back on itself, with this area serving as a hinge. The reenforcement provided by this invention is particularly valuable in that circumstance. The narrow strip portion is relatively narrow with respect to the normal second side edge of the strip. The term is not intended to limit the extent of the outwardly bulging portion of the narrow second side strip portion.

The squeeze clamp of this invention may share in some of the characteristics of the squeeze clamp disclosed in co-pending Utterberg U.S. application Ser. No. 08/943,672, filed Oct. 3, 1997. For example, the squeeze clamp may carry at least one projecting portion, which will be carried by one section of the strip to close and seal the flexible tube carried by the clamp on clamp closing by pressing the tube against another section of strip. A first strip end may define a first latch for engagement and releasable locking with a second latch of a second strip end. The first end may also define a first projection extending toward the second end and having a length that substantially reduces or eliminates a gap between the first and second ends when the clamp is in its open position.

The reduction of such a gap by the first projection can facilitate the mass production assembly of sets using the squeeze clamp, since squeeze clamps in bulk are less likely to hook together in a manner which is time consuming to separate.

Also, the second end of the squeeze clamp can carry a second projection extending outwardly from the second end in a direction which is substantially longitudinal of the direction of extension of tubing carried in the clamp. This can facilitate clamp opening. However, the second projection is out of the way of the fingers of the user while pressing the first end of the clamp into closed position with the second end.

Generally, as the outer diameter of the tube gets bigger, the width of the squeeze clamp needs to be larger and stronger, with needed added strength being provided by the laterally outwardly bulging, narrow strip portion of portions provided by this invention. Available clamps on the market are generally of a width of no more than 12 mm. for a flexible tube with an outer diameter of 4 mm.

DESCRIPTION OF SPECIFIC EMBODIMENTS

Figure 1:
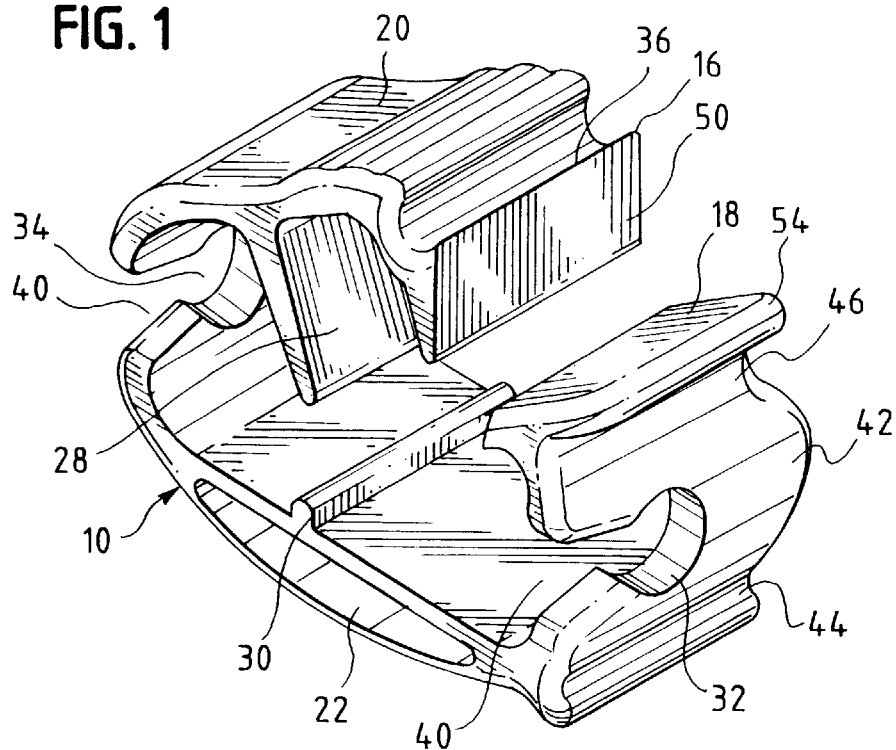
FIG. 1 is a perspective view of the squeeze clamp of this invention in the open position.
Figure 2:
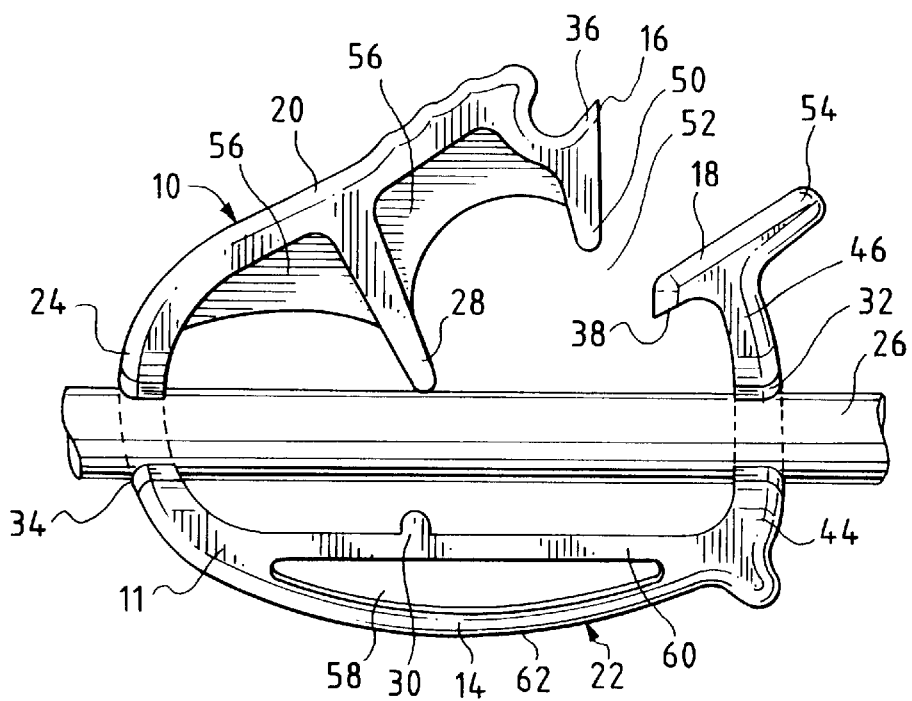
FIG. 2 is a side elevational view of the squeeze clamp of FIG. 1.
Figure 5:
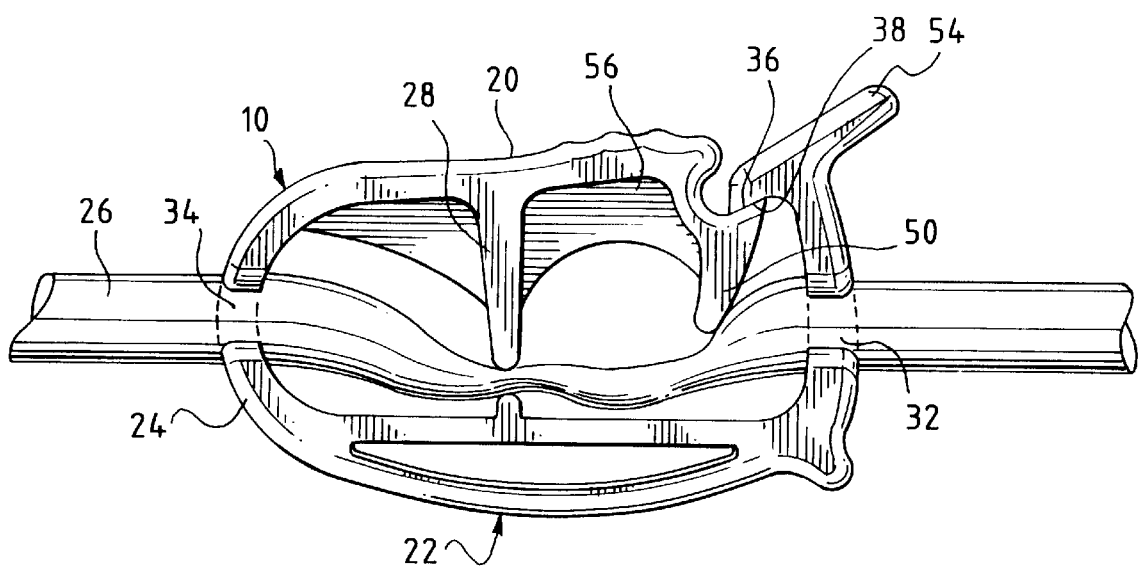
FIG. 5 is a side elevational view of the squeeze clamp of FIG. 2 in the closed position.

Referring to the drawings, squeeze clamp 10 comprises an unitary strip of plastic having first and second opposed side edges 12, 14 (FIG. 3) and first and second ends 16, 18 as best shown in FIG. 2. A plastic strip 11 makes up squeeze clamp 10, being bent back on itself in its natural, unstressed position so that the respective ends 16, 18 are adjacent to each other. Particularly, strip 11 of the clamp comprises, in this embodiment, a pair of relatively straight portions 20, 22 (FIG. 2) separated by a curved, hinge portion 24 which flexes as the squeeze clamp moves by bending and releasing between open and closed positions. The clamp of FIGS. 1–4 is shown in the open position, latching together in the closed position with their ends engaging as shown in FIG. 5. Clamp 10 is shown in FIG. 2 to be carried on flexible tubing of a medical set 26, which is flexible, and may be squeezed shut in conventional manner when the clamp is in the closed position by the near engagement of opposed projections 28, 30.

Clamp 10 also defines a pair of spaced apertures 32, 34 to permit flexible tube 26 to extend through and be carried by the clamp.

Clamp 10 also defines a pair of latches 36, 38, which are configured to engage each other by abutting retention when clamp 10 is bent into the closed position. The clamp has an open position which is typically its natural, unstressed position. Thus, the clamp may be closed by squeezing straight portions 20, 22 together until latch surfaces 36, 38 snap into abutting relation. In this configuration, the two projections 28, 30 squeeze tubing 26 into a closed, fluid tight, sealed configuration, as is generally conventional in clamps of this overall type of design.

Figure 3:
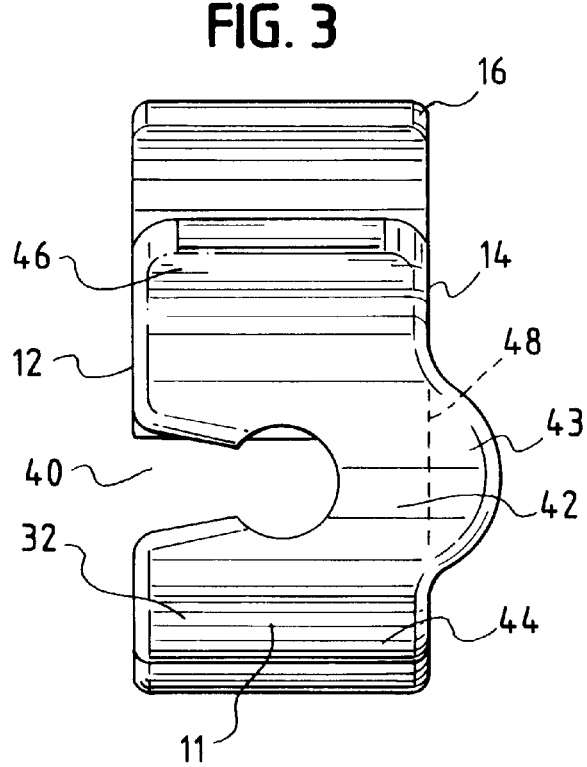
FIG. 3 is a front elevational view of the squeeze clamp of FIG. 1.
Figure 4:
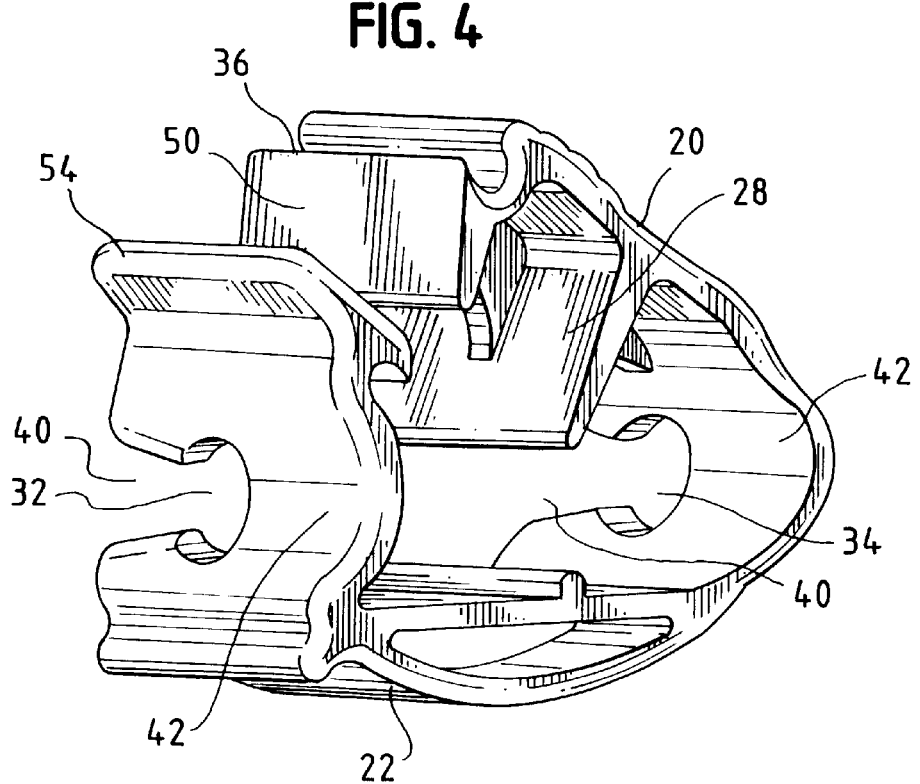
FIG. 4 is a perspective view of the squeeze clamp of FIG. 1 taken from the other side of the clamp.

In accordance with this invention, the respective spaced apertures 32, 34 have lateral slots 40 that each extend through side edge 12 of the strip as shown particularly in FIG. 3. This permits squeeze clamp 10 to be laterally emplaced on tubing 26 at any time, irrespective of whether the ends of tubing 26 are connected or not, for easy installation of such clamps onto tubing sets. Correspondingly, a narrow strip portion 42 is created, relative to the overall width of strip 11 and particularly relative to wider strip portions 44, 46 positioned on either side of narrow strip portion 42.

In accordance with this invention, one, and preferably both, of the narrow strip portions 42 (FIG. 4) extend laterally outwardly beyond second side edge 14 of the rest of strip 11 to form an outward bulge 43. Thus, the width of narrow strip 42 is substantially greater than it would be if it terminated at a straight extension of side edge 14, as indicated by dotted line 48. This extra material in narrow strip portion 42 provides added strength and resistance against undesired torsion or twisting as particularly the clamp is being closed by a nurse in use of a set. On the other hand, the overall width of strip 11 along most of its length is not enlarged, which facilitates the use of a small package of a coiled set carrying the clamps of this invention.

First strip end 16 may also define a first projection 50 extending toward second end 18 and having a length that substantially reduces or eliminates the gap 52 between the first and second ends when the clamp is in its open position. As stated above, this can reduce the likelihood that the clamps in bulk hook together in a manner which is time-consuming to separate on a mass production basis.

Also, second end 18 of clamp 10 can carry a second projection 54, which extends outwardly from second end 18 in a direction which is substantially longitudinal of the direction of extension of tubing carried in the clamp, to facilitate clamp opening. Second projection 54 can thus be out of the way of the fingers of the user, while it serves to aid in opening of the clamp. In this particular embodiment, second projection 54 extends at an acute angle to tube 26 of about 30–45 degrees. This angle is typically reduced a bit when the clamp is in closed position, since second projection 54 is forced to rotate to a certain extent downwardly by the spring action of first end 16, with its latch 36 pressing latch 38 upwardly.

Reinforcing ribs 56 may also be provided to the straight section 20 of strip 11 to provide lateral reinforcement to projection 28.

Aperture 58 is provided between a pair of members 60, 62 that comprise a straight section 22, in order to provide strength with a minimum of plastic.

The above has offered for illustrative purposes only, and is not intended to limit the scope of the invention of this application, which is as defined in the claims below.

That which is claimed:

1. A squeeze clamp for flexible tubing having an open and a closed position, which comprises: a strip of plastic having first and second opposed side edges and first and second ends, said strip being bent back on itself so that said ends are adjacent to each other; said strip defining a pair of spaced apertures to permit a flexible tube to extend through and be carried by said clamp, said apertures extending laterally through the first side edge of said strip, said apertures being each located next to one of a plurality of narrow strip portions, each connected to wider strip portions on either side of said narrow strip portions, at least one of said narrow strip portions extending laterally outwardly, in the plane of said narrow strip portion, beyond the second side edge of substantially the rest of said plastic strip to strengthen said narrow strip portion.

2. The squeeze clamp of claim 1 in which at least one of said narrow strip portions is located adjacent to an area where the strip bends back on itself, said area serving as a hinge.

3. The squeeze clamp of claim 1 which carries at least one projecting portion to close and seal a flexible tube carried by the clamp on clamp closing by pressing said tube against another section of said strip.

4. The squeeze clamp of claim 1 in which said first end defines a first projection extending toward said second end and having a length that substantially reduces or eliminates a gap between the first and second ends when the clamp is in said open position.

5. The squeeze clamp of claim 1 in which a second projection extends outwardly from said second end in a direction which is substantially at an acute angle of no more than about 45 degrees upwardly of the direction of extension of tubing carried in the clamp.

6. A tubing set having a length of tubing which extends through said pair of spaced apertures of the squeeze clamp of claim 1.

7. A squeeze clamp for flexible tubing having open and closed positions, which comprises a strip of plastic having first and second opposed side edges and first and second ends, said strip being bent back on itself so that said ends are adjacent to each other in its natural, unstressed configuration; said strip defining a pair of spaced apertures to permit a flexible tube to extend therethrough and to be carried by said clamp, said apertures extending laterally through the first side edge of said strip, said apertures being each located next to one of a plurality of narrow strip portions, each portion being connected to wider strip portions on either side of said narrow strip portions, at least one of said narrow strip portions extending laterally outwardly, in the plane of said narrow strip portion, beyond the second side edge of the rest of said plastic strip to strengthen said narrow strip portion, in which at least one of said narrow strip portions is located adjacent to an area where the strip bends back on itself, said area serving as a hinge.

8. The squeeze clamp of claim 7 which carries at least one projecting portion to close and seal the flexible tube carried by the clamp on clamp closing, by pressing said tube against another section of said strip.

9. The squeeze clamp of claim 8 in which said first end defines a first projection extending toward said second end and having a length that substantially reduces or eliminates a gap between the first and second ends when the clamp is in open position.

10. The squeeze clamp of claim 9 in which a second projection extends outwardly from said second end in a direction which is substantially at an acute angle of substantially no more than about 45 degrees upwardly of the direction of extension of tubing carried in the clamp.

11. A tubing set having a length of tubing which extends through said pair of spaced apertures of the squeeze clamp of claim 10.

* * * * *